(12) United States Patent
Donovan (10) Patent No.: US 8,961,525 B2
(45) Date of Patent: Feb. 24, 2015

(54) INFLATABLE BONE TAMP WITH PREDETERMINED EXTENSIBILITY

(75) Inventor: Brian W. Donovan, San Jose, CA (US)

(73) Assignee: Kyphon Sarl, Neuchatel (CH)

( * ) Notice: Subject to any disclaimer, the term of this patent is extended or adjusted under 35 U.S.C. 154(b) by 78 days.

(21) Appl. No.: 13/016,884

(22) Filed: Jan. 28, 2011

(65) Prior Publication Data
US 2012/0197321 A1 Aug. 2, 2012

(51) Int. Cl.
A61B 17/56 (2006.01)
A61B 17/88 (2006.01)
A61B 17/34 (2006.01)
A61B 17/00 (2006.01)

(52) U.S. Cl.
CPC ......... *A61B 17/8805* (2013.01); *A61B 17/8811* (2013.01); *A61B 17/8855* (2013.01); *A61B 17/3472* (2013.01); *A61B 2017/00867* (2013.01)
USPC .......................... 606/86 R; 606/105; 606/192

(58) Field of Classification Search
USPC ....... 606/63, 86 R, 92–94, 99, 105, 191–200; 623/17.12; 604/99.01–99.04
See application file for complete search history.

(56) References Cited

U.S. PATENT DOCUMENTS

| 4,029,099 | A | * | 6/1977 | Fifield | 604/326 |
|---|---|---|---|---|---|
| 4,318,410 | A | * | 3/1982 | Chin | 606/194 |
| 5,843,116 | A | | 12/1998 | Crocker et al. | |
| 5,944,691 | A | * | 8/1999 | Querns et al. | 604/104 |
| 6,129,737 | A | | 10/2000 | Hamilton et al. | |
| 6,364,900 | B1 | | 4/2002 | Heuser | |
| 6,416,457 | B1 | | 7/2002 | Urik et al. | |
| 6,527,739 | B1 | | 3/2003 | Bigus et al. | |
| 6,719,773 | B1 | * | 4/2004 | Boucher et al. | 606/192 |
| 2002/0138128 | A1 | * | 9/2002 | Stiger et al. | 623/1.11 |
| 2003/0130664 | A1 | | 7/2003 | Boucher et al. | |
| 2005/0038382 | A1 | * | 2/2005 | Miller et al. | 604/103.1 |
| 2008/0065091 | A1 | * | 3/2008 | Scribner et al. | 606/94 |
| 2008/0215031 | A1 | * | 9/2008 | Belfort et al. | 604/500 |
| 2009/0024087 | A1 | * | 1/2009 | Kennedy et al. | 604/99.01 |
| 2009/0088788 | A1 | | 4/2009 | Mouw | |
| 2009/0247945 | A1 | * | 10/2009 | Levit et al. | 604/103 |
| 2009/0312807 | A1 | * | 12/2009 | Boudreault et al. | 606/86 R |

FOREIGN PATENT DOCUMENTS

| DE | 10010467 A1 | 9/2001 |
|---|---|---|
| WO | WO2006053312 A1 | 5/2006 |
| WO | WO2008026888 A1 | 3/2008 |

* cited by examiner

*Primary Examiner* — Christian Sevilla
*Assistant Examiner* — Eric S Gibson
(74) *Attorney, Agent, or Firm* — Sorell Lenna & Schmidt LLP (57) ABSTRACT

An inflatable bone tamp for performing a minimally invasive surgical procedure includes an inner shaft that incorporates a longitudinally extensible section. The predetermined longitudinally extensible section permits greater control over the elongation of the inflatable portion of the inflatable bone tamp, thereby allowing performance characteristics to be tailored to specific procedures and/or situations. The predetermined longitudinally extensible section can be implemented in various ways, such as a spring, elastomer, or mechanical linkage, among others.

21 Claims, 12 Drawing Sheets

INFLATABLE BONE TAMP WITH PREDETERMINED EXTENSIBILITY

FIELD OF THE INVENTION

The invention relates to a system and method for performing a surgical procedure, and in particular, to an inflatable device that exhibits controlled longitudinal growth during inflation.

BACKGROUND OF THE INVENTION

A minimally invasive procedure is a medical procedure that is performed through the skin or an anatomical opening. In contrast to an open procedure for the same purpose, a minimally invasive procedure will generally be less traumatic to the patient and result in a reduced recovery period.

However, there are numerous challenges that minimally invasive procedures present. For example, minimally invasive procedures are typically more time-consuming than their open procedure analogues due to the challenges of working within a constrained operative pathway. In addition, without direct visual feedback into the operative location, accurately selecting, sizing, placing, and/or applying minimally invasive surgical instruments and/or treatment materials/devices can be difficult.

For example, for many individuals in our aging world population, undiagnosed and/or untreatable bone strength losses have weakened these individuals' bones to a point that even normal daily activities pose a significant threat of fracture. In one common scenario, when the bones of the spine are sufficiently weakened, the compressive forces in the spine can cause fracture and/or deformation of the vertebral bodies. For sufficiently weakened bone, even normal daily activities like walking down steps or carrying groceries can cause a collapse of one or more spinal bones. A fracture of the vertebral body in this manner is typically referred to as a vertebral compression fracture. Other commonly occurring fractures resulting from weakened bones can include hip, wrist, knee and ankle fractures, to name a few.

Fractures such as vertebral compression fractures often result in episodes of pain that are chronic and intense. Aside from the pain caused by the fracture itself, the involvement of the spinal column can result in pinched and/or damaged nerves, causing paralysis, loss of function, and intense pain which radiates throughout the patient's body. Even where nerves are not affected, however, the intense pain associated with all types of fractures is debilitating, resulting in a great deal of stress, impaired mobility and other long-term consequences. For example, progressive spinal fractures can, over time, cause serious deformation of the spine ("kyphosis"), giving an individual a hunched-back appearance, and can also result in significantly reduced lung capacity and increased mortality.

Because patients with these problems are typically older, and often suffer from various other significant health complications, many of these individuals are unable to tolerate invasive surgery. Therefore, in an effort to more effectively and directly treat vertebral compression fractures, minimally invasive techniques such as vertebroplasty and, subsequently, kyphoplasty, have been developed. Vertebroplasty involves the injection of a flowable reinforcing material, usually polymethylmethacrylate (PMMA—commonly known as bone cement), into a fractured, weakened, or diseased vertebral body. Shortly after injection, the liquid filling material hardens or polymerizes, desirably supporting the vertebral body internally, alleviating pain and preventing further collapse of the injected vertebral body.

Because the liquid bone cement naturally follows the path of least resistance within bone, and because the small-diameter needles used to deliver bone cement in vertebroplasty procedure require either high delivery pressures and/or less viscous bone cements, ensuring that the bone cement remains within the already compromised vertebral body is a significant concern in vertebroplasty procedures. Kyphoplasty addresses this issue by first creating a cavity within the vertebral body (e.g., with an inflatable balloon) and then filling that cavity with bone filler material. The cavity provides a natural containment region that minimizes the risk of bone filler material escape from the vertebral body. An additional benefit of kyphoplasty is that the creation of the cavity can also restore the original height of the vertebral body, further enhancing the benefit of the procedure.

Conventional inflatable bone tamps (IBTs) used in kyphoplasty procedures incorporate balloon catheters that are constructed using two coaxial catheters, with the distal ends of the outer and inner catheters being coupled to the proximal and distal end regions, respectively, of the balloon. Because the inner catheter has a relatively small diameter, during inflation of the balloon, the inner catheter exhibits a degree of longitudinal (i.e., axial) growth, thereby allowing the balloon to grow longitudinally as well.

For many applications, such as use in a kyphoplasty procedure, this longitudinal balloon growth can be beneficial. For example, if the inner catheter is completely inextensible (i.e., cannot extend longitudinally), the balloon inflation will be rather spherical, which in turn can undesirably create local regions of high pressure at the apex(es) of the sphere. On the other hand, if the inner catheter elongation is completely unconstrained, the balloon may not exhibit sufficient radial expansion. Ideally, the limited-elongation expansion profile enabled by a controllably extensible inner catheter can reduce the risk of localized high pressure regions by creating a "flatter", more oval-shaped inflation profile, while still allowing radial growth sufficient to achieve desired procedure outcomes.

However, because of the variations inherent in catheter manufacturing, it can be difficult to control/predict the extensibility of the inner catheter within a balloon catheter. Historically, this aspect of balloon catheter performance has been of little significance, but the advent of higher pressure applications (such as use in kyphoplasty and other bone environments) has increased the importance of well-defined control over balloon catheter longitudinal growth.

Accordingly, it is desirable to provide surgical tools and techniques that enable controlled longitudinal growth of a balloon catheter during inflation.

SUMMARY OF THE INVENTION

By providing an inflatable bone tamp with an inner shaft having at least one region that is substantially more extensible than the other region(s) of the inner shaft, a predetermined degree of longitudinal balloon growth can be incorporated into the inflatable bone tamp to achieve a desired inflation profile.

In one embodiment, an inflatable bone tamp can include outer shaft, an inner shaft disposed within the outer shaft, and an inflatable structure having proximal and distal ends coupled to the distal ends of the outer shaft and the inner shaft, respectively. The inner shaft can include one or more predetermined regions that are substantially more longitudinally extensible than the remainder of the inner shaft (i.e., one or more regions that provide substantially all of the elongation of the inner shaft when the inner shaft is placed in tension).

In some embodiments, the longitudinally extensible region(s) of the inner shaft can incorporate resilient elements (i.e., structures that resiliently return to an original length, such as springs, elastomers, and resilient mechanical linkages, among others). In various other embodiments, the longitudinally extensible region(s) of the inner shaft can incorporate non-resilient elements (i.e., structures that do not inherently return to an original length, such as plastically deforming structures/features and friction joints, among others).

In some embodiments, the portions of the inner shaft that are not longitudinally extensible can be formed from various metal wire/rod materials (e.g., stainless steel or nitinol) or from substantially non-compliant catheter materials (e.g., nylon or polyethylene). Similarly, in various embodiments, the inflatable structure can be formed from any material, and can take any desired configuration (e.g., single chamber, multi-lobe, multi-balloon, etc).

In various other embodiments, a surgical procedure for treating a compromised bone structure (e.g., a vertebral compression fracture, tibial plateau fracture, a calcaneus fracture, a proximal humerus fracture, a distal radius fracture, or a femoral head fracture, among others) can be performed by creating an access path (e.g., using a cannula), inserting an inflatable bone tamp having an inner shaft with a predetermined region(s) of extensibility into a target bone (e.g., a fractured vertebra) via the access path, inflating the bone tamp causing the region(s) of extensibility to lengthen, thereby allowing the inflatable portion of the bone tamp to correspondingly elongate during expansion, the expansion creating a cavity in cancellous bone and optionally restoring the original cortical bone profile (e.g., restore vertebral body height), deflating and removing the inflatable bone tamp, and then filling the cavity with bone filler material to support the treated bone.

In a procedure such as kyphoplasty, the inflatable structure elongation enabled by the region(s) of extensibility can allow the inflation force of the bone tamp to be more broadly distributed across the endplates of the fractured vertebra. This in turn can improve the ability of the bone tamp to restore the height of the vertebra, while minimizing the risk of endplate breach due to localized inflation forces.

In another embodiment, a surgical system for treating bone can include one or more inflatable bone tamps incorporating inner shafts having localized regions of predetermined extensibility. The surgical system can further include additional equipment for performing a surgical procedure using the inflatable bone tamp(s) (e.g., one or more cannulas sized to accept the inflatable bone tamps, access tools such as drills, guide wires, obturators, trocars, and/or curettes) and/or instructions for performing the surgical procedure using the one or more inflatable bone tamps.

As will be realized by those of skilled in the art, many different embodiments of an inflatable bone tamp incorporating an inner shaft having a predetermined extensible region(s), and systems, kits, and/or methods of using such an inflatable bone tamp according to the present invention are possible. Additional uses, advantages, and features of the invention are set forth in the illustrative embodiments discussed in the detailed description herein and will become more apparent to those skilled in the art upon examination of the following.

DETAILED DESCRIPTION

By providing an inflatable bone tamp with an inner shaft having at least one region that is substantially more extensible than the other region(s) of the inner shaft, a predetermined degree of longitudinal balloon growth can be incorporated into the inflatable bone tamp to achieve a desired inflation profile.

Figure 1A:
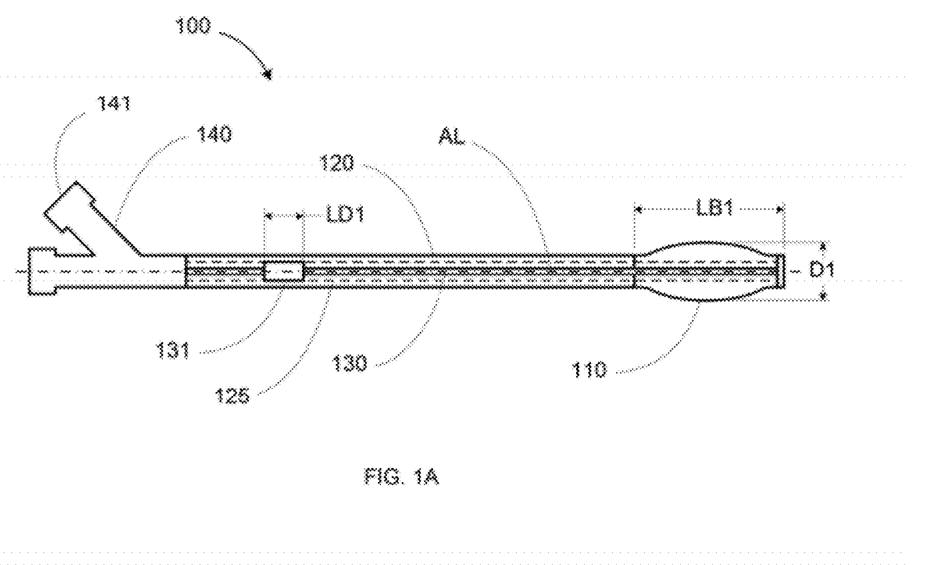
FIGS. 1A-1B show an exemplary inflatable bone tamp incorporating an inner shaft having a localized extensible region.

FIG. 1A shows an embodiment of an inflatable bone tamp 100 that includes an inflatable structure 110, an outer shaft 120, an inner shaft 130 disposed at least partially within outer shaft 120, and a connector 140. The proximal end regions of inner shaft 130 and outer shaft 120 are coupled to connector 140, while the distal end regions of inner shaft 130 and outer shaft 120 are coupled to the distal and proximal end regions, respectively, of inflatable structure 110.

In one embodiment, inflatable structure 110 can be inflated through a lumen formed between outer shaft 120 and inner shaft 130 (e.g., using inflation fluid delivered via connector 140). In another embodiment, inner shaft 130 can itself be a catheter for delivering the inflation fluid to inflatable structure 110. And in another embodiment, inflatable bone tamp 100 can include an optional additional inner catheter 125 (indicated by dashed lines) for defining an inflation fluid flow path (either between catheter 125 and outer shaft 120, between catheter 125 and inner shaft 130, or within catheter 125).

Inner shaft 130 includes an extensible element 131 that is substantially more longitudinally extensible than the remainder of inner shaft 130. In particular, as described in greater detail below, extensible element 131 is configured such that during normal usage of inflatable bone tamp 100, any elongation of inner shaft 130 along longitudinal axis AL will occur at extensible element 131, rather than at other portions of inner shaft 130.

Figure 1B:
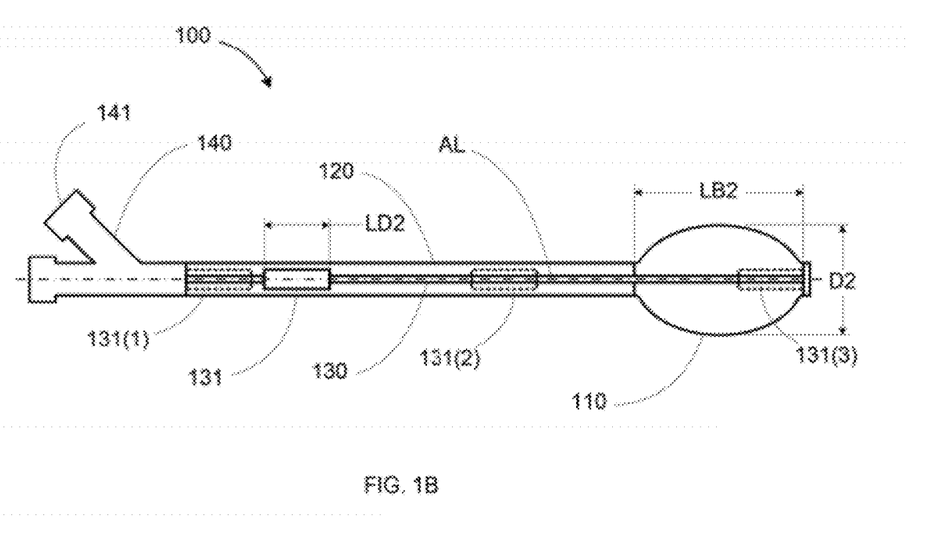

Thus, as inflatable element 110 expands as shown in FIG. 1B, the resulting tension along longitudinal axis AL causes extensible element 131 to lengthen along axis AL, which in turn allows inflatable element 110 to grow longitudinally as well. Note that while a single extensible element 131 is described and depicted for exemplary purposes, inner shaft 130 can include any number of extensible elements 131, as indicated by optional additional extensible elements 131(1), 131(2), and 131(3) shown in FIG. 1B. Note further that extensible element(s) 131 can be positioned anywhere along inner shaft 130, including at the proximal end of inner shaft 130 (e.g., extensible element 131(1) and/or the distal end of inner shaft 130 (e.g., extensible element 131(3)).

To maximize control over the amount of longitudinal growth allowed for inflatable element 110, extensible element 131 can be selected and/or configured to be substantially more extensible than the rest of inner shaft 130. In such embodiments, any longitudinal growth exhibited by inflatable element 110 during use would be enabled by corresponding longitudinal growth in extensible element 130.

For example, as indicated in FIG. 1A, in an "at rest" condition, when inflatable element 110 is in an inflated, non-distended state (e.g., prior to the point at which inflatable structure 110 begins to exert any longitudinal force on inner shaft assembly 130), extensible element 131 can have a length LD1, and inflatable structure 110 can have a length LB1. As inflatable structure 110 is further inflated, extensible element 131 elongates to a length LD2, thereby allowing inflatable element 110 to elongate to a length LB2. When extensible element 131 is substantially more extensible than the rest of inner shaft 131, the elongation of extensible element 131 will be substantially equal to the elongation of inflatable element 110 (i.e., LD2−LD1 substantially equal to LB2−LB1).

Figure 3A:
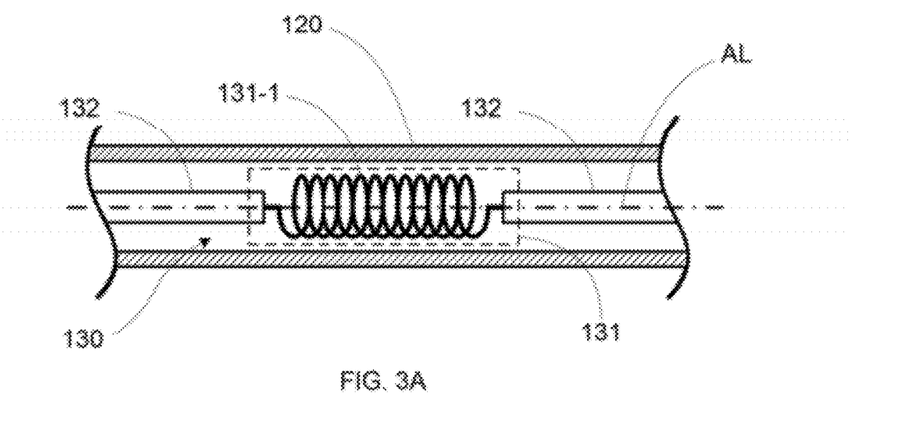
FIGS. 3A-3E show exemplary embodiments of localized extensible regions for the inflatable bone tamp of FIGS. 1A-1B.

Extensible element 131 can be any structure providing the desired amount of longitudinal extension for inflatable bone tamp 100. In various embodiments, extensible element 131 can be resiliently extensible along the longitudinal axis AL during inflation of inflatable element 110. For example, in FIG. 3A shows an exemplary embodiment of extensible element 131 that includes a spring 131-1 coupling substantially inextensible portions 132 (e.g., stainless steel or nitinol wire or rod, nylon-based catheter, or any other structure having greater longitudinal stiffness than extensible element 131) of inner shaft 130. As inflatable structure 110 (not shown) is inflated and begins to expand, tension along longitudinal axis AL causes spring 131-1 to extend (lengthen), thereby allowing longitudinal extension of inflatable structure 110.

Figure 3B:
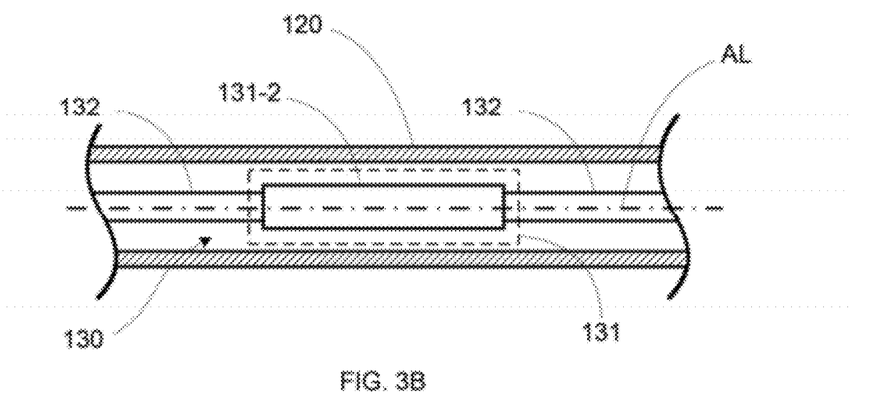
Figure 3C:
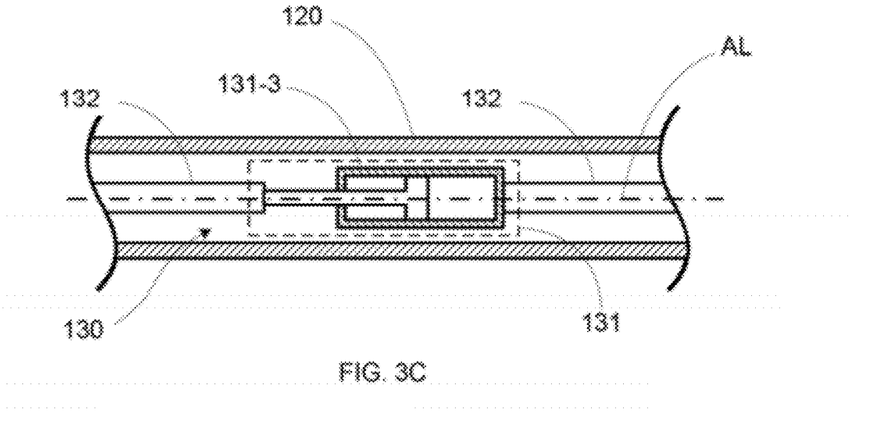

In another embodiment shown in FIG. 3B, extensible element 131 can incorporate an elastomeric material (e.g., polyurethane, rubber, or any other elastic material) connecting the relatively inextensible portions 132 of inner shaft 130. In another embodiment shown in FIG. 3C, extensible element 131 can incorporate a hydraulic or pneumatic system (e.g., cylinder) 131-3 connecting the relatively inextensible portions 132 of inner shaft 130.

Figure 3D:
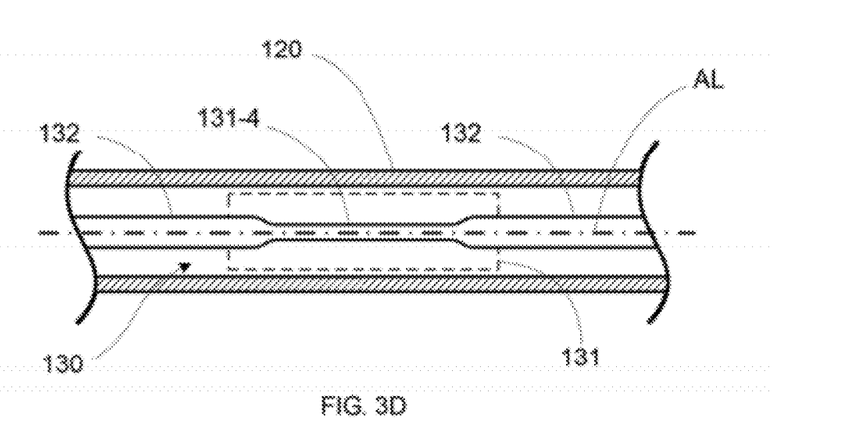

In various other embodiments, extensible element 131 can non-resiliently extensible along the longitudinal axis AL during inflation of inflatable element 110. For example, in an embodiment shown in FIG. 3D, extensible element 131 can incorporate a reduced thickness region 131-4 sized to plastically deform in response to tensile loading of inner shaft 130. Note that in various other embodiments, a reduced thickness region 131-4 could provide a region of elastic deformation (e.g., if inner shaft 130 is a polyurethane catheter).

Figure 3E:
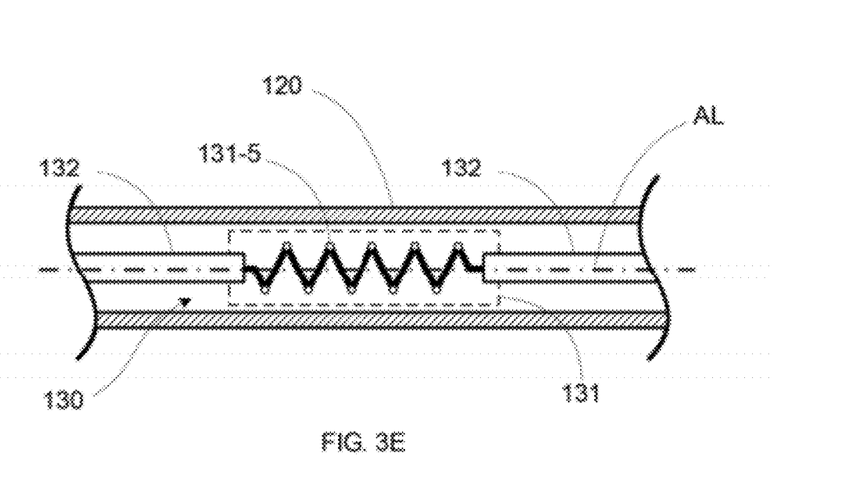

In another embodiment shown in FIG. 3E, extensible element 131 can include a mechanical linkage 131-5. In various embodiments, mechanical linkage 131-5 can provide resilient extension capabilities (e.g., spring-loaded and/or incorporating flexible linkage elements), and in various other embodiments, mechanical linkage 131-5 can provide non-resilient extension capabilities (e.g., friction joints or bellows system).

Returning to FIGS. 1A and 1B, note that while inflatable structure 110 is depicted as a simple, single lobed balloon for exemplary purposes, in various other embodiments, inflatable structure 110 can take any form that would benefit from the lengthening capability provided by inner shaft 130.

Figure 4A:
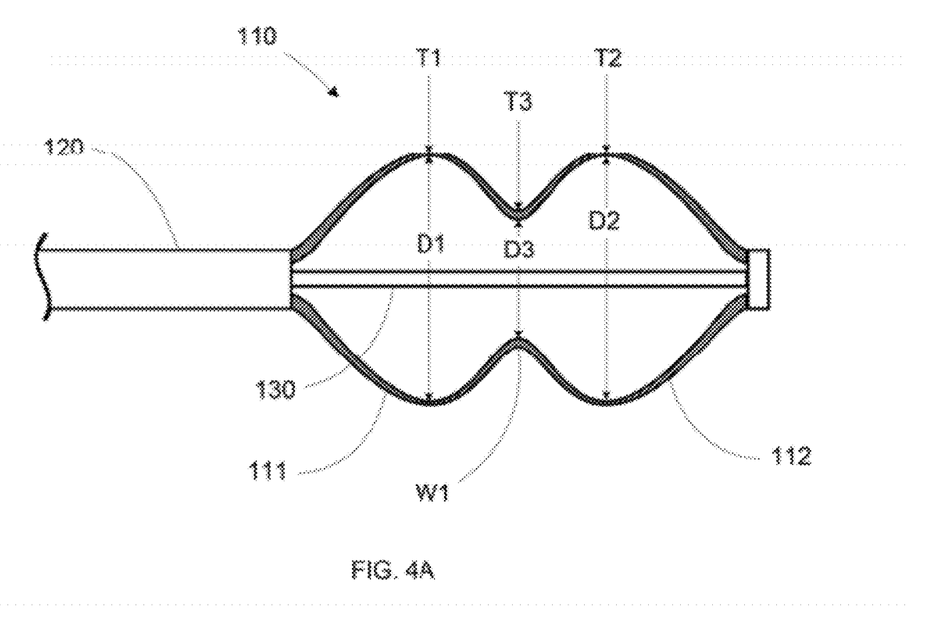
FIGS. 4A-4B show exemplary inflatable structures for the inflatable bone tamp of FIGS. 1A-1B.

For example, FIG. 4A shows an exemplary "peanut-shaped" balloon what that includes two lobes 111 and 112 joined at a narrowed waist W1 (i.e., maximum non-distended (i.e., non-stretched) diameters D1 and D2 of lobes 111 and 112, respectively, are greater than the minimum diameter D3 of waist W1). The peanut shape can beneficially result in a more ovoid inflation profile that can enhance the performance of the inflatable bone tamp. The inflation profile can be further enhanced by controlling the wall thickness profile of inflatable structure 110 (e.g., by forming waist W1 to have a maximum thickness T3 that is greater than the minimum thickness T1 and T2 of lobes 111 and 112, respectively.

Figure 4B:
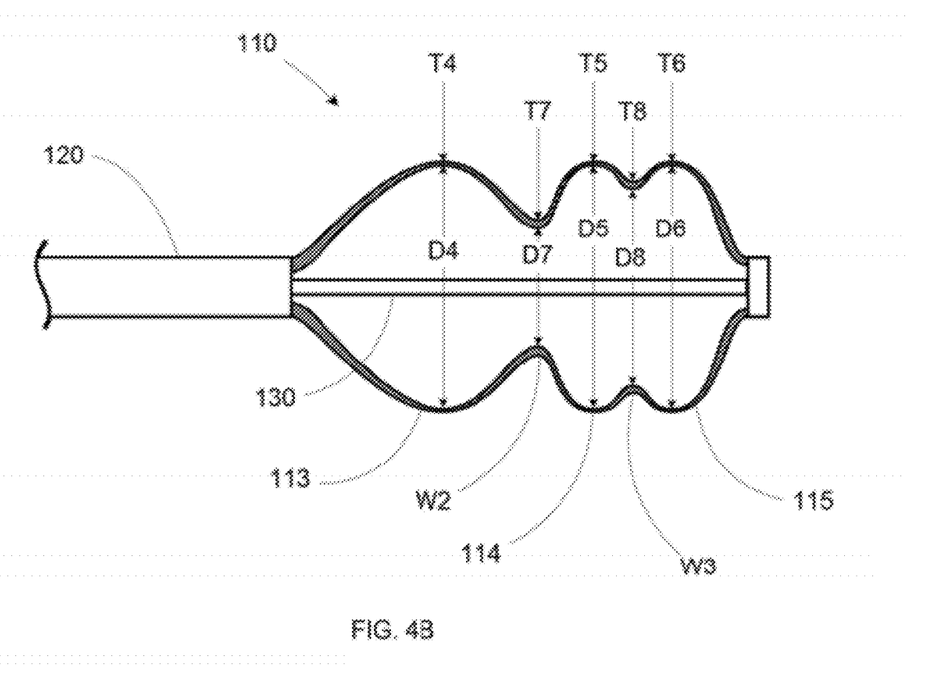

FIG. 4B shows another exemplary balloon construction for inflatable structure 110 that includes lobes 113 and 114 joined at a narrowed waist W2 (i.e., maximum non-distended diameters D4 and D5 greater than the minimum diameter D7 of waist W2), and an additional lobe 115 joined to lobe 114 at a second narrowed waist W3 (i.e., maximum non-distended diameters D5 and D6 greater than the minimum diameter D8 of waist W3). The multi-lobe configuration shown in FIG. 4B can result in an inflation profile exhibiting an outwardly tapering inflation profile, such that the maximum distended diameter of inflatable structure 110 occurs towards the distal end of inflatable structure 110, which can beneficially enhance performance during certain procedures, such as kyphoplasty. Various other balloon configurations will be readily apparent (e.g., multi-chambered, multi-balloon, and/or various shapes, among others).

Figure 2A:
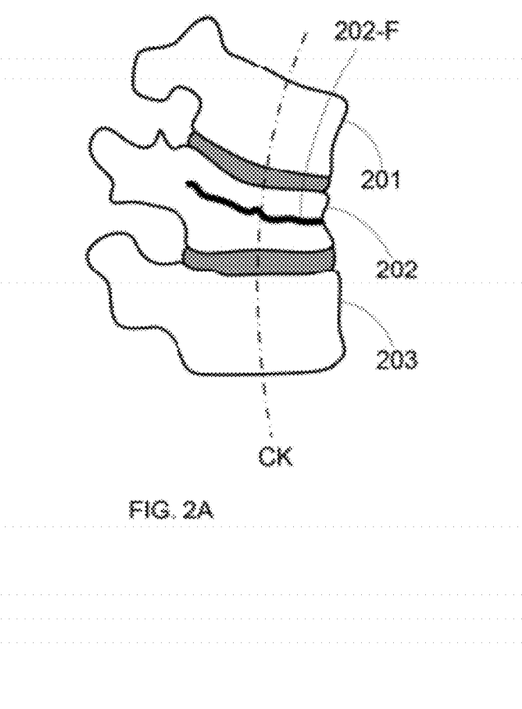
FIGS. 2A-2G show an exemplary surgical procedure that incorporates the inflatable bone tamp of FIGS. 1A-1B.

FIGS. 2A-2G show an exemplary surgical procedure (kyphoplasty) that involves the use of an inflatable bone tamp incorporating in inner shaft having an extensible element. FIG. 2A shows a portion of a human vertebral column having vertebrae 201, 202, and 203. Vertebra 202 has collapsed due to a vertebral compression fracture (VCF) 202-F that could be the result of osteoporosis, cancer-related weakening of the bone, and/or physical trauma. The abnormal curvature CK of the spine caused by VCF 202-F can lead to severe pain and further fracturing of adjacent vertebral bodies.

Figure 2B:
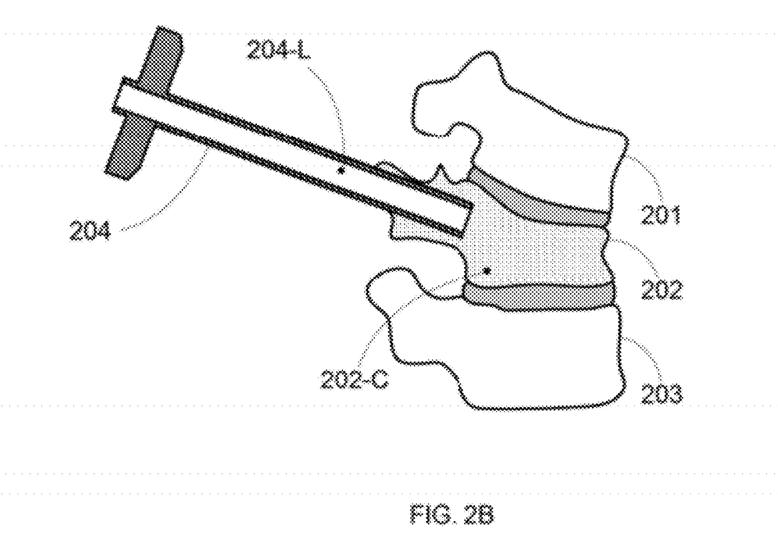

FIG. 2B shows a cannula 204 being positioned next to the target surgical location, which in this case is the cancellous bone structure 202-C within fractured vertebra 202. In this manner, a percutaneous path to vertebra 202 is provided via an interior lumen 204-L of cannula 204. Typically, cannula 204 is docked into the exterior wall of the vertebral body (using either a transpedicular or extrapedicular approach) using a guide needle and/or dissector, after which a drill or other access tool (not shown) is used to create a path further into the cancellous bone 202-C of vertebra 202. However, any other method of cannula placement can be used to position cannula 204.

Figure 2C:
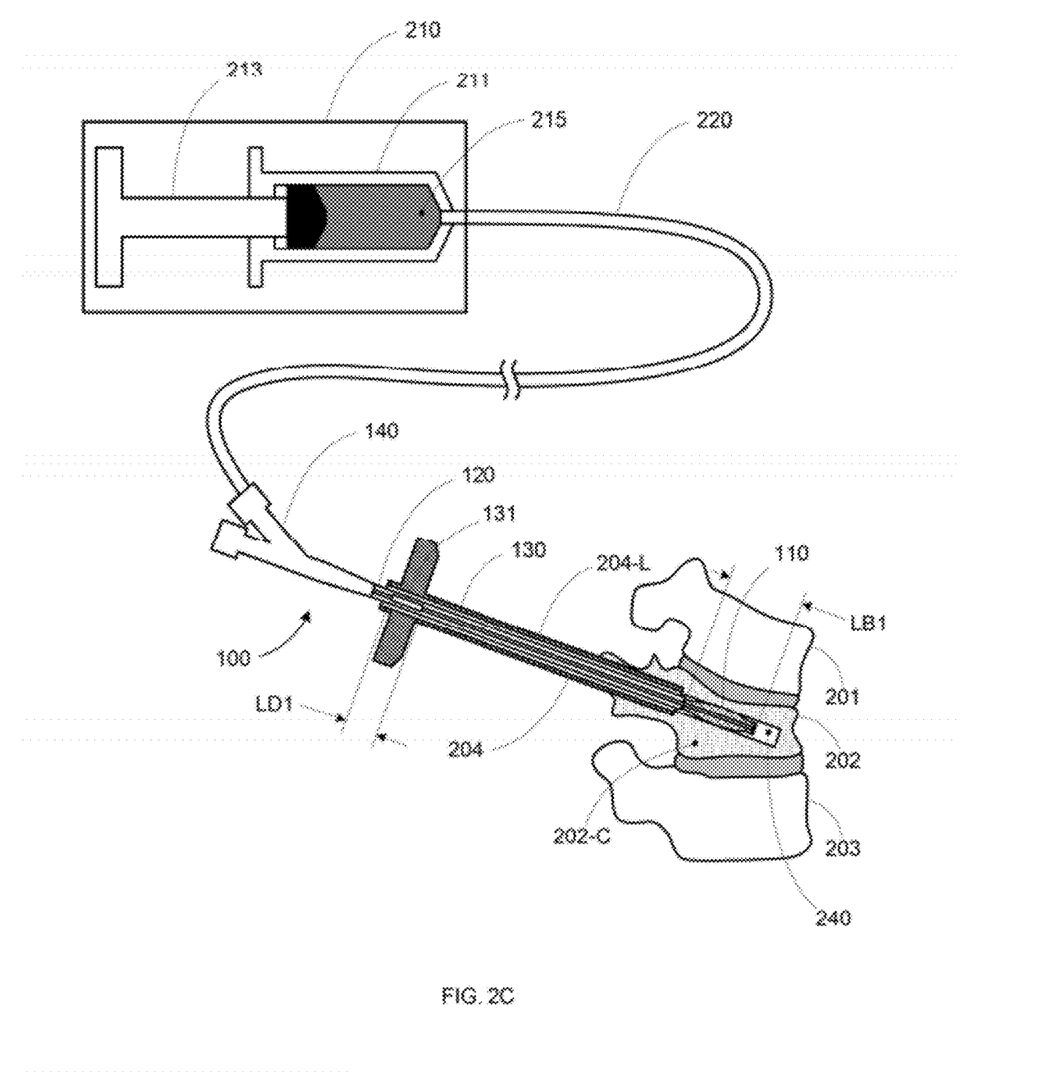

Then in FIG. 2C, an inflatable bone tamp 100 (as described with respect to FIGS. 1A-1B) is placed into cannula 204. Inflatable bone tamp 100 is coupled to an inflation mechanism 210 by a flow channel 220 (e.g., flexible tubing). For exemplary purposes, inflation mechanism 210 is depicted as a syringe having a plunger 213 for expressing inflation fluid 215 (e.g., saline solution, air, contrast solution, or any other fluid) from a barrel 211. Note that in various other embodiments, inflation mechanism 210 can be any system for delivering inflation, such as a syringe, pump, or compressed gas system, among others. Furthermore, in various other embodiments, inflation mechanism 210 can be directly connected to inflatable bone tamp 100.

Figure 2D:
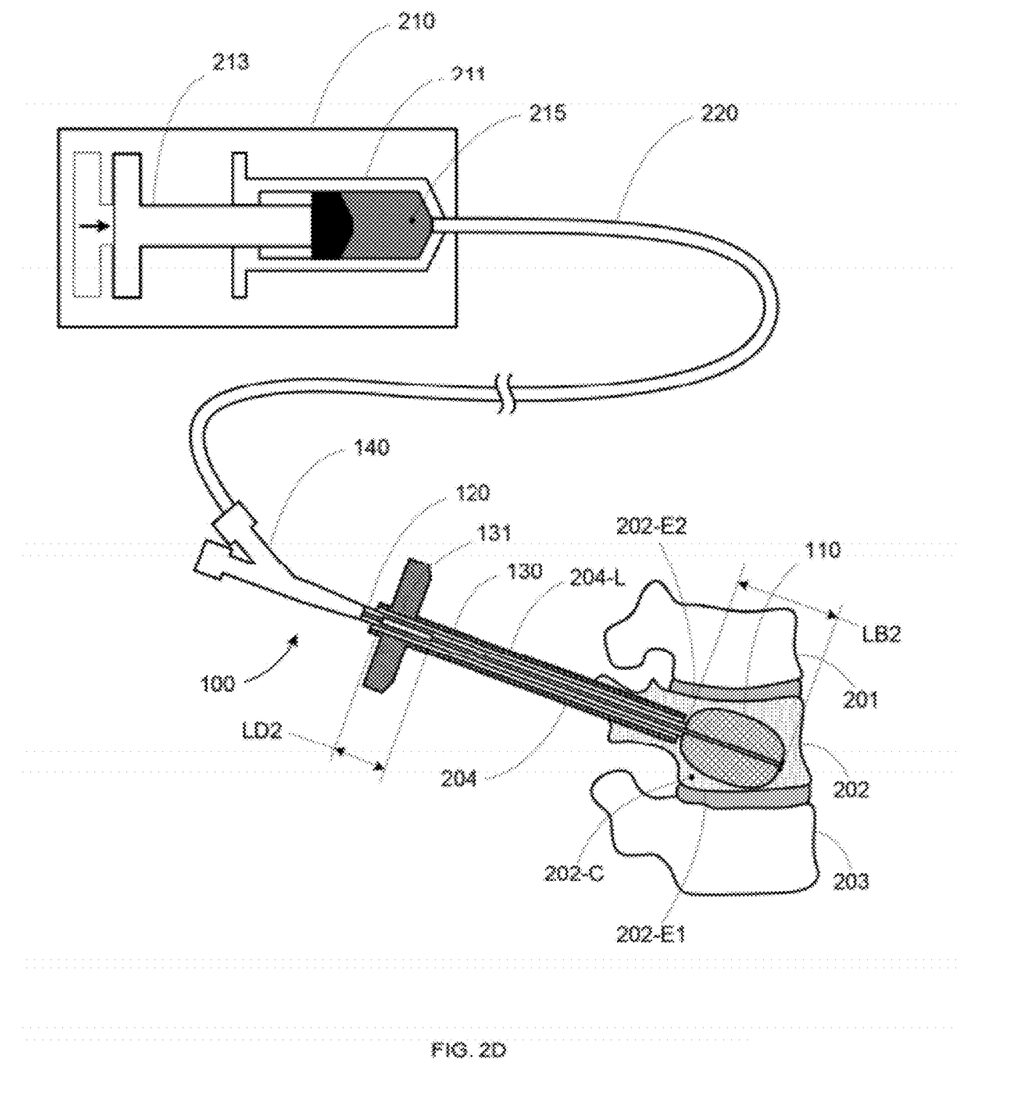

As noted above, inflatable bone tamp 100 includes an inner shaft 130 having an extensible element 131 that allows inner shaft 130 to elongate under tension. As inflation mechanism 210 is actuated to drive inflation fluid 215 into inflatable structure 110, inflatable structure 110 begins to expand within fractured vertebra 202. For example, in the embodiment shown in FIG. 2D, a force is applied to drive plunger 213 through barrel 211, thereby expressing inflation fluid 215 through flow channel 220, connector 140, outer shaft 120 and/or inner shaft 130, and into inflatable structure 110. The resulting expansion of inflatable structure 110 initially compresses the surrounding cancellous bone 202-C to begin creating a cavity within vertebra 202, and can also push apart the harder endplates 202-E1 (inferior) and 202-E2 (superior) of vertebra 202 apart, thereby increasing the likelihood of successful height restoration of fractured vertebra 202, as shown in FIG. 2D.

As described above with respect to FIGS. 1A-1B, the expansion of inflatable structure 110 creates a longitudinal force along inner shaft 130, which causes extensible element 131 to lengthen from an original length LD1 to an extended length LD2, which in turn allows inflatable structure 110 to similarly elongate (from an original length LB1 to an extended length LB2). The resulting inflation profile for inflatable structure 110 (i.e., a more elongate inflation profile than would be achieved with a rigidly constrained length for inflatable structure 110; but with greater radial growth than would be achieved without any length restraint on inflatable structure 110) can distribute the loading applied to endplates 202-E1 and 202-E1, and thereby reduce the possibility of breaching those endplates.

Figure 2E:
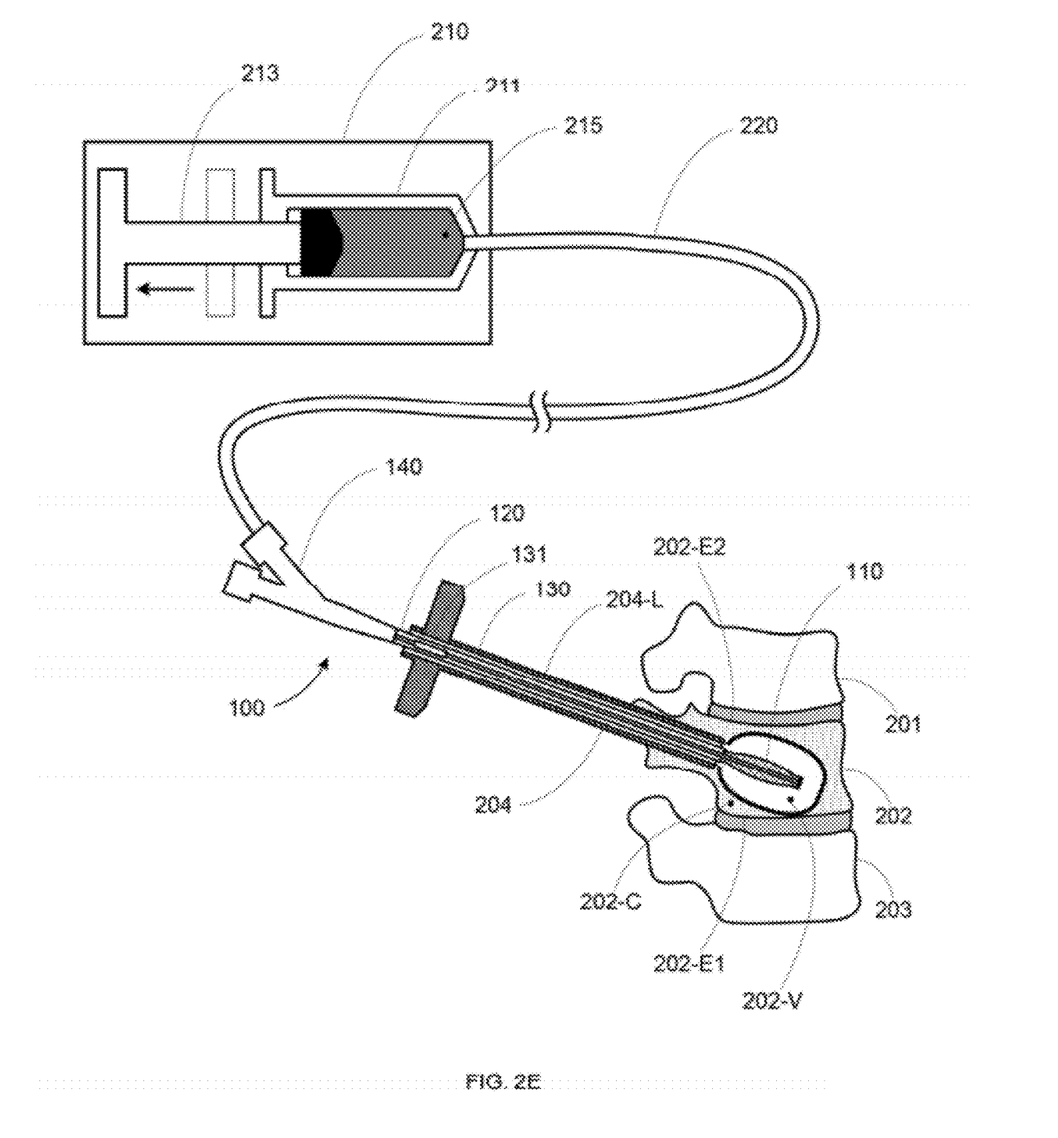

Once inflatable structure 110 has been expanded to a desired volume and/or a desired height restoration has been achieved in vertebra 202, inflatable structure 110 is deflated, leaving a well-defined cavity 202-V, as shown in FIG. 2E. Note that in some embodiments, an elastic deformable extensible element 131 can return to its original length, thereby "pulling" inflatable structure 110 back of its original length as well. In various other embodiments, a plastically deformable extensible element 131 can result in the deflated inflatable structure 110 remaining in a partially or fully elongated condition.

Figure 2F:
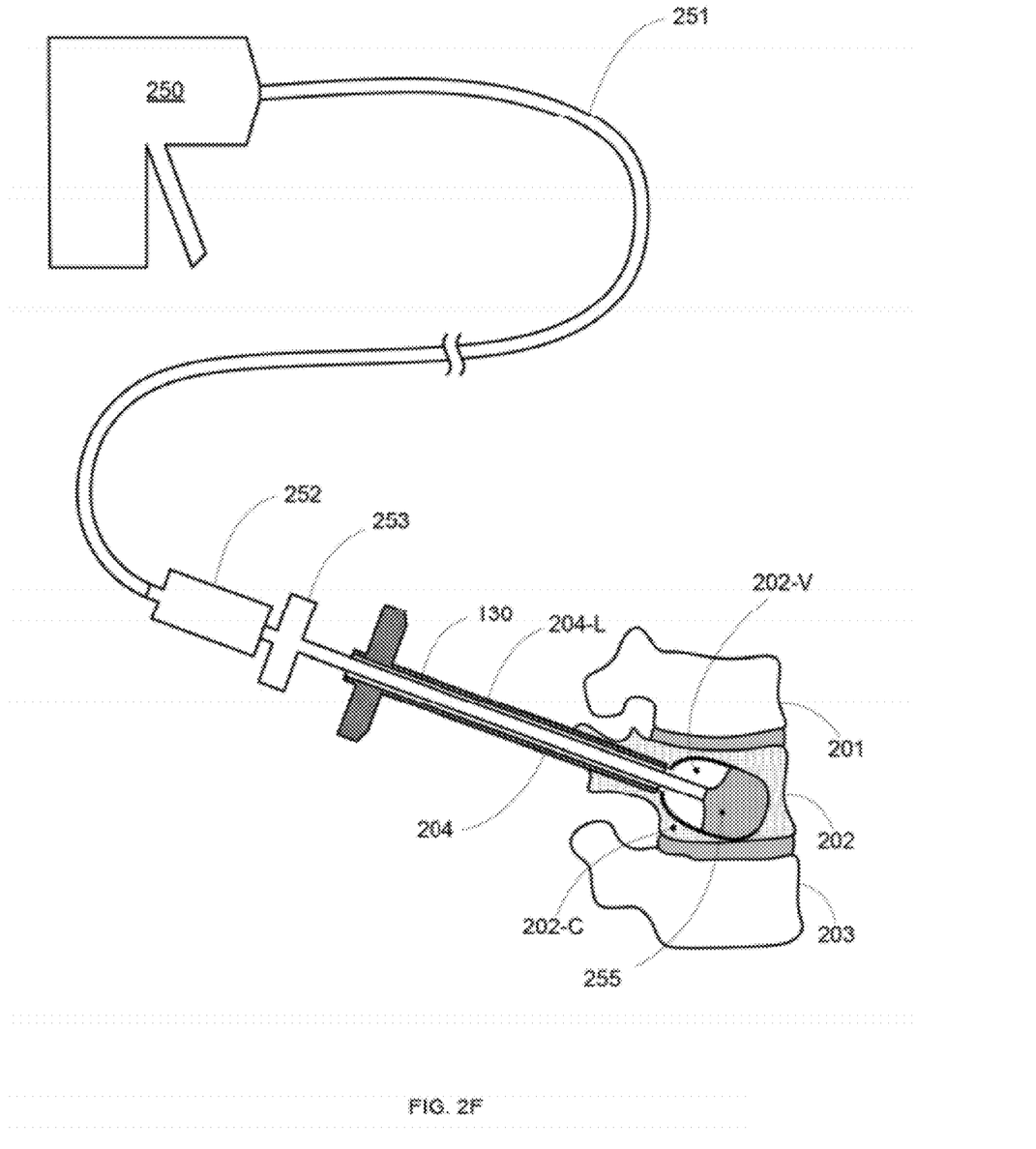

Inflatable bone tamp 100 can then be removed from cannula 204, and bone filler material (e.g., PMMA) can be delivered into cavity 202-V. As shown in FIG. 2F, a delivery nozzle 253 can be inserted through cannula 204 and into cavity 202-V, and can be used to direct bone filler material 255 into cavity 202-V. In some embodiments, a quantity of bone filler material 255 can be housed in a cartridge 252 attached to delivery nozzle 253. A hydraulic actuator 250 can then be used to remotely express bone filler material 255 from cartridge 252 via a hydraulic line 251 (e.g., cartridge 252 can include a piston that is driven by the hydraulic pressure supplied by hydraulic line 251).

Note, however, that in various other embodiments, bone filler material 255 can be delivered to cavity 202-V in any number of different ways (e.g., a high pressure cement delivery pump that delivers the cement to nozzle 253 through a flexible line, or a syringe or other delivery device filled with bone filler material 255 that is attached directly to nozzle 253, or even directly to cannula 204). In addition, in various other embodiments, bone filler material 255 can be delivered in multiple portions of the same or different materials (e.g., a bone cement followed by a biologic agent).

Figure 2G:
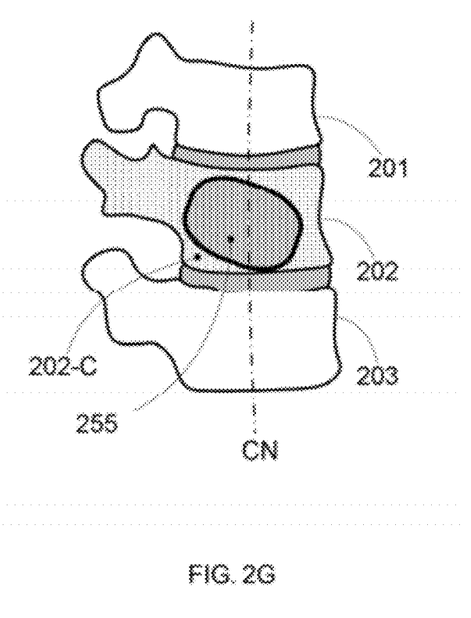

Once the filling operation is complete, delivery nozzle 253 and cannula 204 are removed from vertebra 202 (and the patient's body) as shown in FIG. 2G. Upon hardening, bone filler material 255 provides structural support for vertebra 202, thereby substantially restoring the structural integrity of the bone and the proper musculoskeletal alignment of the spine. As shown in FIG. 2G, due to the restoration of height in fractured vertebra 202, the abnormal curvature CK shown in FIG. 2A is corrected to a normal curvature CN. In this manner, the pain and attendant side effects of a vertebral compression fracture can be addressed by a minimally invasive kyphoplasty procedure.

Note that although a kyphoplasty procedure is depicted and described for exemplary purposes, inflatable bone tamp 100 can be similarly used in any other target surgical location in or around bone, such as a tibial plateau fracture, a proximal humerus fracture, a distal radius fracture, a calcaneus fracture, or a femoral head fracture, among others. For example, to restore a tibial plateau fracture, the extensibility of extensible element(s) 131 could be decreased to increase radial expansion and provide more localized lifting (e.g., for a Type I fracture), or could be increased to create a more elongated expansion profile for a more distributed lift surface area (e.g., for a Type III fracture). Various other usages will be readily apparent.

Figure 5:
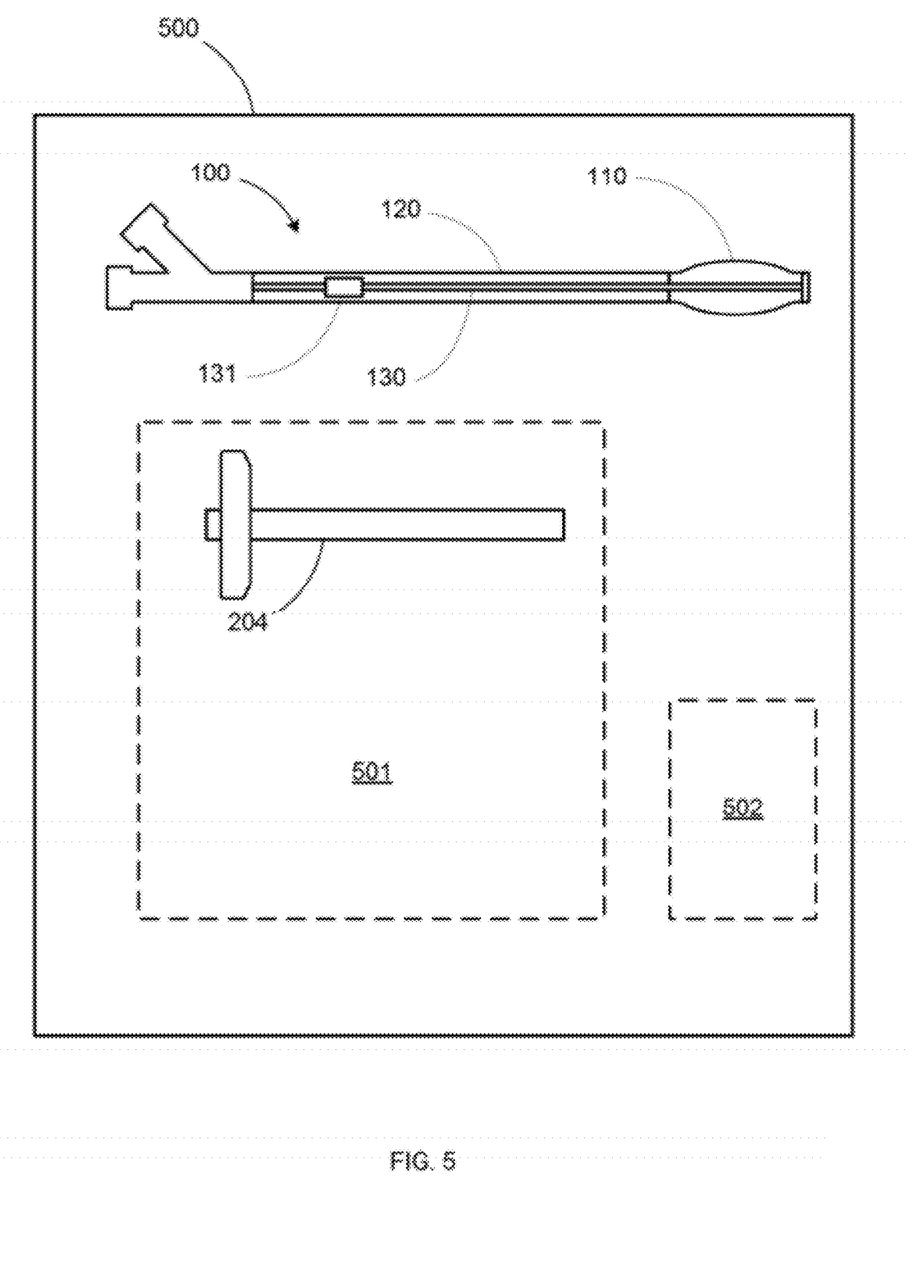
FIG. 5 shows a kit that includes the inflatable bone tamp of FIGS. 1A-1B.

FIG. 5 shows a diagram of a kit 500 for use in performing a surgical procedure, such as the kyphoplasty procedure described with respect to FIGS. 2A-2G above. Kit 500 includes an inflatable bone tamp 100 (e.g., as described above with respect to FIGS. 1A-1B and 2A-2G) having an inner shaft 130 with an extensible region 131. In various embodiments, kit 500 can further include optional additional instruments 501, such as a cannula 204 sized to receive inflatable bone tamp 100, an introducer, guide pin, drill, curette, and/or access needle, among others (only cannula 204 is shown for clarity). In various other embodiments, kit 500 can further include optional directions for use 502 that provide instructions for using inflatable bone tamp and optional additional instruments 501 (e.g., instructions for performing a surgical procedure using inflatable bone tamp 100 and optional additional instruments 501, such as described with respect to FIGS. 2A-2G).

Figure 6:
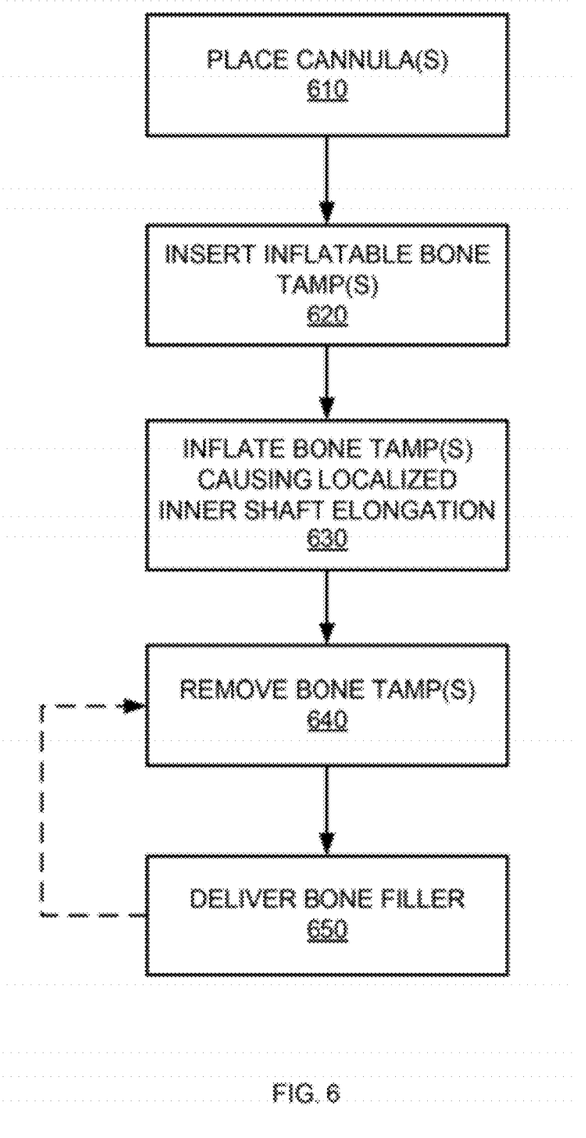
FIG. 6 shows a flow diagram for a surgical procedure that makes use of the inflatable bone tamp of FIGS. 1A-1B.

FIG. 6 shows a flow diagram of a process for performing a surgical procedure such as kyphoplasty using an inflatable bone tamp including an inflatable bone tamp that allows controlled longitudinal growth, as described with respect to FIG. 1A-1B. In a PLACE CANNULA(S) step 610, a cannula is positioned within a patient to provide a path to a target surgical location (e.g., as described with respect to FIG. 2B). Note that although a unilateral procedure is described above for clarity, in various other embodiments, a bilateral procedure can be used (e.g., placing two cannulas to provide access through both pedicles of a vertebra).

Then, in an INSERT INFLATABLE BONE TAMP(S) step 620, an inflatable bone tamp including an extensible element 131 (e.g., as described with respect to FIGS. 1A-1B) is placed within the patient through the cannula (e.g., as described with respect to FIG. 2C). Note once again that if multiple cannulas have been placed in step 610, an inflatable bone tamp can be inserted into each cannula.

Next, in an INFLATE BONE TAMP(S) CAUSING LOCALIZED INNER SHAFT ELONGATION step 630, the inflatable bone tamp(s) is (are) inflated to create a cavity in cancellous bone and, ideally, at least partially restore the original cortical bone profile (e.g., as described with respect to FIGS. 2C and 2D). As described above, the inflatable bone tamp lengthens during inflation, thereby enhancing the performance of the inflatable bone tamp during the kyphoplasty procedure as described above. Note that if multiple inflatable bone tamps have been introduced in step 620, their inflation can be sequential, simultaneous, sequentially incremental (e.g., partially inflating one before partially or fully inflating another), or any other order.

The inflatable bone tamp is then deflated and withdrawn from the patient in a REMOVE BONE TAMP step 640 (e.g., as described with respect to FIG. 2E), and in a DELIVER BONE FILLER step 650, a bone filler material (e.g., bone cement) is conveyed to the cavity formed by the inflatable bone tamp to create a permanent reinforcing structure within the bone (e.g., as described with respect to FIGS. 2F and 2G).

Note that if multiple bone tamps have been placed within the patient (e.g., in a bilateral procedure) in step 620, one or more of those inflatable bone tamps can be left (inflated) within the patient to provide support for the bone structure during subsequent material delivery during step 650. The process can then loop back to step 640 and then step 650 until all inflatable bone tamps have been removed, and all the resulting cavities in the bone have been filled with bone filler material.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A device for performing a surgical procedure, the device comprising:
    an inflatable bone tamp comprising:
        an outer shaft;
        an inner shaft including a proximal end comprising at least a first inextensible region and a second inextensible region disposed within the outer shaft;
        an inflatable structure having a proximal end coupled to a distal end of the outer shaft and a distal end coupled to a distal end of the inner shaft, the inflatable structure having an initial length and an inflated length, the inflatable structure being configured to compress surrounding cancellous bone to create a cavity within vertebra and push apart endplates of the vertebra when the inflatable structure has the inflated length; and
        an extensible element positioned within the outer shaft coupling the first region and the second region, the extensible element having an initial length and a predetermined expanded length and is configured to change in length as the inflatable structure is inflated and deflated, wherein a difference between the initial length and the predetermined expanded length of the extensible element is equal to a difference between the initial length and the inflated length of the inflatable structure.

2. The device of claim 1, wherein the extensible element comprises a resilient element.

3. The device of claim 2, wherein the resilient element comprises a spring.

4. The device of claim 2, wherein the resilient element comprises an elastomer.

5. The device of claim 1, wherein the extensible element is non-resilient.

6. The device of claim 1, wherein the first region and the second region comprise a wire formed from at least one of stainless steel and nitinol, wherein the extensible element comprises the wire, wherein in the first region and the second region the wire has a first diameter, wherein in the extensible element the wire has a second diameter, and wherein the first diameter is greater than the second diameter.

7. The device of claim 1, wherein the inner shaft further comprises a second extensible element positioned at the distal end of the inner shaft, the second extensible element being more longitudinally extensible than the first region.

8. The device of claim 1, wherein the extensible element comprises a first portion and a second portion, the first portion being fixed relative to the second inextensible region, the first portion comprising an inner surface defining a chamber, the second portion being movably disposed in the chamber.

9. The device of claim 1, further comprising an inner catheter positioned within the outer shaft such that the inner shaft extends through the inner catheter, wherein a space between the inner catheter and the outer shaft defines an inflation lumen that is in communication with an interior of the inflatable structure.

10. The device of claim 1, wherein the inflatable bone tamp comprises a plurality of lobes, adjacent lobes being joined at a narrow waist.

11. A surgical kit comprising:
    a cannula defining an access lumen; and
    an inflatable bone tamp sized to pass through the access lumen, the inflatable bone tamp comprising:
        an outer shaft;
        an inner shaft having a proximal end including a first inextensible region and second inextensible region disposed within the outer shaft; and
        an inflatable structure coupled between a distal end of the outer shaft and a distal end of the inner shaft that is opposite the proximal end, the inflatable structure having an initial length and an inflated length, the inflatable structure being configured to compress surrounding cancellous bone to create a cavity within vertebra and push apart endplates of the vertebra when the inflatable structure has the inflated length; and
        a longitudinally extensible element positioned within the outer shaft coupling the first region and the second region, the extensible element having an initial length and a predetermined expanded length and is configured to change in length as the inflatable structure is inflated and deflated, wherein a difference between the initial length and the predetermined expanded length of the extensible region is equal to a difference between the initial length and the inflated length of the inflatable structure,
    wherein the longitudinally extensible element being configured to allow longitudinal growth of the inflatable structure during inflation of the inflatable structure.

12. The surgical kit of claim 11, wherein the first and second inextensible regions each comprise at least one of a stainless steel wire and a nitinol wire, and wherein the at least one of the stainless steel wire and the nitinol wire is connected to a distal end of the inflatable structure.

13. The surgical kit of claim 11, wherein the longitudinally extensible element comprises at least one of a spring, an elastomer, a linkage, a hydraulic cylinder, and a pneumatic cylinder.

14. The surgical kit of claim 11, wherein the inner shaft further comprises a second longitudinally extensible element positioned at the distal end of the inner shaft.

15. The surgical kit of claim 11, further comprising instructions for performing a kyphoplasty procedure using the inflatable bone tamp.

16. The device of claim 11, wherein the inflatable bone tamp comprises a plurality of lobes, adjacent lobes being joined at a narrow waist.

17. A method comprising:
creating an access path to a bone structure comprising cancellous bone;
providing an inflatable bone tamp comprising an outer shaft, an inner shaft comprising a proximal end including at least a first inextensible region and a second inextensible region disposed within the outer shaft, and an inflatable structure coupled between the outer shaft and the inner shaft, the inflatable structure having an initial length and an inflated length, the inner shaft comprising an extensible element positioned within the outer shaft coupling the first region and the second region, the extensible element having an initial length and a predetermined expanded length and configured to change in length as the inflatable structure inflates and deflates, wherein a difference between the initial length and the predetermined expanded length of the extensible element is equal to a difference between the initial length and the inflated length of the inflatable structure,
inserting the inflatable bone tamp into the access path to position the inflatable structure within the bone structure; and
inflating the inflatable structure to compress a portion of the cancellous bone and create a cavity,
wherein inflating the inflatable structure causes longitudinal elongation of only a predetermined portion of the inner shaft.

18. The method of claim 17, wherein the predetermined portion of the inner shaft comprises at least one of a spring, an elastomer, a linkage, a hydraulic cylinder, and a pneumatic cylinder.

19. The method of claim 17, further comprising deflating the inflatable structure, wherein deflating the inflatable structure causes longitudinal shortening of the predetermined portion of the inner shaft.

20. The method of claim 17, further comprising delivering a bone filler material into the cavity through the access path.

21. The method of claim 20, wherein creating the access path comprises docking a cannula with the bone structure, and wherein delivering the bone filler material comprises inserting a delivery nozzle into the cannula and injecting the bone filler material into the cavity from the delivery nozzle.

* * * * *

UNITED STATES PATENT AND TRADEMARK OFFICE
CERTIFICATE OF CORRECTION

| | | |
|---|---|---|
| PATENT NO. | : 8,961,525 B2 | Page 1 of 1 |
| APPLICATION NO. | : 13/016884 | |
| DATED | : February 24, 2015 | |
| INVENTOR(S) | : Donovan | |

It is certified that error appears in the above-identified patent and that said Letters Patent is hereby corrected as shown below:

In the Specification

In Column 4, Line 59, delete "131(1)" and insert -- 131(1)) --, therefor.

In Column 4, Line 67, delete "extensible element 130." and insert -- extensible element 131. --, therefor.

In Column 5, Line 11, delete "inner shaft 131," and insert -- inner shaft 130, --, therefor.

In Column 5, Line 67, delete "(e.g.," and insert -- e.g., --, therefor.

In Column 7, Line 13, delete "110;" and insert -- 110, --, therefor.

In the Claims

In Column 10, Line 65, in Claim 16, delete "device" and insert -- surgical kit --, therefor.

Signed and Sealed this
Eleventh Day of August, 2015

Michelle K. Lee
*Director of the United States Patent and Trademark Office*